(12) United States Patent
Wu et al.

(10) Patent No.: US 9,290,801 B2
(45) Date of Patent: Mar. 22, 2016

(54) DETECTION METHOD OF MICRO-RNA WITH HIGH SPECIFICITY

(75) Inventors: Hongfei Wu, Shanghai (CN); Honghoi Ting, Shanghai (CN); Zuxun Gong, Shanghai (CN); Ruoying Tan, Shanghai (CN)

(73) Assignee: BIOVUE TECHNOLOGY LTD, Shanghai (CN)

( * ) Notice: Subject to any disclaimer, the term of this patent is extended or adjusted under 35 U.S.C. 154(b) by 48 days.

(21) Appl. No.: 14/001,267

(22) PCT Filed: Dec. 8, 2011

(86) PCT No.: PCT/CN2011/083724
§ 371 (c)(1),
(2), (4) Date: Sep. 29, 2013

(87) PCT Pub. No.: WO2012/119471
PCT Pub. Date: Sep. 13, 2012

(65) Prior Publication Data
US 2014/0295434 A1   Oct. 2, 2014

(30) Foreign Application Priority Data
Mar. 8, 2011   (CN) .......................... 2011 1 0054104

(51) Int. Cl.
*C12Q 1/68*   (2006.01)
(52) U.S. Cl.
CPC .............. *C12Q 1/686* (2013.01); *C12Q 1/6848* (2013.01); *C12Q 1/6851* (2013.01)
(58) Field of Classification Search
None
See application file for complete search history.

(56) References Cited

U.S. PATENT DOCUMENTS

2005/0272075 A1 *   12/2005   Jacobsen et al. .................. 435/6

FOREIGN PATENT DOCUMENTS

WO   WO2008092016 A2   7/2008

OTHER PUBLICATIONS

Exiqon (miRCURY LNA™ Universal RT microRNA PCR, attached, Oct. 27, 2009).*
Exiqon (hereinafter "Exigon2"; miRCURY LNA™ Universal RT microRNA PCR Manual, attached, Jul. 2010).*
Andreasen et al. (Improved microRNA quantification in total RNA from clinical samples, Methods. Apr. 2010;50(4):S6-9).*
Diffenbach et al. (General Concepts for PCR Primer Design, PCR Methods Appl. Dec. 1993;3(3):S30-7).*
Tabone et al. (Temperature Switch PCR (TSP): Robust assay design for reliable amplification and genotyping of SNPs, BMC Genomics. Dec. 3, 2009;10:580).*
Kibbe (OligoCalc: an online oligonucleotide properties calculator, Nucleic Acids Res. Jul. 2007;35(Web Server issue):W43-6. Epub Apr. 22, 2007).*
OligoCalc (Oligo Calc: Oligonucleotide Properties Calculator, attached, Jun. 2, 2002, available at http://www.basic.northwestern.edu/ biotools/oligocalc.html).*
Mao et al. (Characterization of EvaGreen and the implication of its physicochemical properties for qPCR applications, BMC Biotechnol. 2007; 7: 76, Published online Nov. 9, 2007).*
Biotechniques_2005: vol. 39, No. 4 (2005): Facile means for quantifying microRNA. Rui Shi and Vincent L. Chiang.
BMC_BIOTECHNOLOGY: BMC Biotechnology 2007, 7:76. Characterization of EvaGreen and the implication of etc . . . Fei Mao. Published: Nov. 9, 2007.
China_Biotechnology 2010, 30 (11): 88/93.

* cited by examiner

*Primary Examiner* — Stephanie K Mummert
*Assistant Examiner* — Aaron Priest
(74) *Attorney, Agent, or Firm* — Adam Bell; Matthew Kaser (57) ABSTRACT

The invention provides a method for detecting miRNA based on polymerase chain reaction comprising EvaGreen dye, and the use of EvaGreen dye in elevating the binding specificity of primers to templates in PCR.

9 Claims, 4 Drawing Sheets

DETECTION METHOD OF MICRO-RNA WITH HIGH SPECIFICITY

The present application is a U.S. national phase application of PCT/CN2011/083724 filed under 35 U.S.C. 371 and claims priority from CN201110054104.7 filed on Mar. 8, 2011, which is hereby incorporated by reference for all purposes.

FIELD OF THE INVENTION

This invention relates to biomedical science, genetic engineering and detection, more specifically, to a detection method for microRNA with high specificity. The method could be used to detect non-coding RNA, thereby describing the condition or status of some diseases.

BACKGROUND OF THE INVENTION

MicroRNAs (miRNAs) are a group of newly discovered non-coding RNAs and can modulate transcription and stability of certain or some target mRNAs by binding to 3's non-coding regions (3's UTRs) of the complementary antisense mRNA thereof in a sequence-specific manner.

Most of miRNAs, such as let-7 RNA, miR-1, miR-34, miR-60, and miR-87, are highly conservative in invertebrates and vertebrates, implicating that they may recognize multiple sites and (or) multiple target sequences of genes with conservative function.

Another subclass of miRNA, small temporal RNA (stRNA, such as lin-4 and let-7), has been was identified based on the analysis on the genome of *Caenorhabditis elegans*. stRNA plays important role in the process of regulating development, such as neuron regeneration, Dauer larva formation, vulva formation, and the terminal differentiation of hypodermal cells.

miRNAs are typically formed by the excision of folded RNA precursors of 60-70 nucleotides. Some miRNAs can be detected upon expression, while some detected only at the peak of expression.

Generally, only one of the strands of hairpin structure was excised and accumulated, presumably because miRNA precursors could be protected by binding proteins thereof against degradation. It is conjectured that these binding proteins may modulate the translational suppression of miRNA. Mature miRNAs can not be formed from the miRNA precursors unless Dicer RNase III and enzymes of Argonaute family are involved in the reaction.

MicroRNAs play important roles in many biological events such as growth, fission, differentiation, development, apoptosis and diseases. Up to now, more than 1200 microRNAs have been discovered in human cells. These miRNAs are involved in regulating more than 60% genes in human.

miRNAs are important biomarkers for the classification of tumors, diagnosis, prediction of diseases and assessment of prognosis. Tumor-associated miRNAs in serum or plasma have been served as biomarkers for tumor diagnosis. The detection and quantification of miRNA are important tools for the discovery of some target genes and pathways, study on disease mechanism, assessment of drug safety and efficacy, disease diagnosis and prognosis. Thus, it is very important to determine the amount of each miRNA in specific cells.

In some cases, it is more important to quantify miRNA, for example, compare levels of miRNA in different tissues or compare the change of miRNA in tissue before and after application of an external cause (a chemical or physical treatment). Because miRNA family with similar sequence will be present in the same cell, it is important to have a detection method with high sensitivity and good specificity. Moreover, it may be beneficial to have methods suitable for high throughput screening samples, e.g. homogeneous methods, and multiplexed methods.

Nowadays, a number of miRNA quantitative analysis methods have been developed, including miRNA chip arrays, SYBR Green® I-based miRNA qRT-PCR assays (Raymond, C. K., Roberts, B. S., Garrett-Engele, P., Lim, L. P., and Johnson, J. M (2005) Simple, quantitative primer-extension PCR assay for direct monitoring of microRNAs and short-interfering RNAs. RNA 11), stem-loop-based TaqMan assays (Chen C, Ridzon D A, Broomer A J, Zhou Z, Lee D H, Nguyen J T, Barbisin M, Xu N L, Mahuvakar V R, Andersen M R, Lao K Q, Livak K J, Guegler K J. 2005. Real-time quantification of microRNAs by stem-loop RT-PCR. Nucleic Acids Res 33(20):e179), beads-based assays, high throughput sequencing and the like. However, each of aforementioned methods has defects. For example, hybridization-based assays (microarray or micro-beads) suffer from low sensitivity and specificity; SYBR-Green® I-based methods suffer from high background and poor specificity; the specificity of stem-loop TaqMan assays is acceptable, however, it is expensive, time-consuming and suffers from deviation, so that it is difficult to be applied in high throughput screen.

EvaGreen® is a double strand DNA-binding dye, exhibiting low PCR inhibition, good melt curve, high thermal and light stability, non-mutagenicity and non-cytotoxicity. EvaGreen® has been used in the determination of melt curve and fluorescent quantitative PCR (Mao F, Leung W Y, Xin X. 2007. Characterization of EvaGreen® and the implication of its physicochemical properties for qPCR applications. BMC Biotechnol. 9; 7:76).

EvaGreen®-based PCR reaction liquids can be obtained from many companies, such as BioRad, Qiagen, Agilent and so on, and many labs have reported the use of EvaGreen™-based reaction liquids prepared in-house, however, there is no report or suggestion that EvaGreen® can improve specificity of reaction.

Summing up, there is no cost effective miRNA detection method available with high sensitivity and specificity.

SUMMARY OF THE INVENTION

The subject of the present invention is to provide a cost effective miRNA detection method with high sensitivity and specificity.

In the first aspect of the present invention, a method for miRNA detection is provided, comprising the following steps:

(a) adding a polyA tail to the 3' end of miRNA for a miRNA sample to be detected;

(b) adding a primer which is complementary or substantially complementary to the polyA tail of miRNA to anneal the primer with miRNA containing the added polyA tail;

(c) reverse-transcribing the miRNA containing the added polyA tail into cDNA;

(d) conducting PCR amplification to the cDNA, using forward and reverse primers complementary to the cDNA in a PCR reaction system containing EvaGreen® fluorescent dye, thereby forming double stranded DNA-EvaGreen® fluorescent dye complex; and detecting the presence and/or the amount of the amplified products during or after the amplification to determine the presence and/or the amount of miRNA to be detected.

In another preferred embodiment, the detection includes qualitative detection and quantitative detection.

In another preferred embodiment, the detection includes the quantitative detection of miRNA by detecting fluorescence intensity.

In another preferred embodiment, the miRNA sample to be detected is RNA extracted from a sample to be detected.

In another preferred embodiment, the exacted RNA is total RNA extracted from a sample either containing or not containing miRNA.

In another preferred embodiment, in step (d), the presence or the amount of the amplified products is determined by detecting the fluorescence value of EvaGreen® dye.

In another preferred embodiment, the forward primer has the following characteristics:

(i) the sequence of 3' end of the forward primer is the same or substantially the same as that of 5' end of the miRNA to be detected; and the Tm value of the sequence of 3' end with cDNA is 45-65° C.;

(ii) the sequence of 5' end of the forward primer makes the Tm value of the whole forward primer with cDNA reach 45-75° C.; and (iii) the length of the forward primer is 8-50 bp.

In another preferred embodiment, the reverse primer has the following characteristics:

(i) 3' end of the reverse primer contains a first complementary region that is complementary to the sequence of 3' end of miRNA to be detected and consists of 0 to 15 bases;

(ii) the middle sequence of the reverse primer is polyT having 8 to 30 bases in length;

(iii) the sequence of 5' end of the reverse primer makes the Tm value of the whole reverse primer with cDNA reach 45-75° C.; and (iv) the length of the reverse primer is 12-50 bp.

In another preferred embodiment, the sample to be detected is selected the following group: animal sample, food, fodder and medicament.

In another preferred embodiment, the sample to be detected is selected the following group: body fluid, dairy product, vegetable, meat, meat products, or water.

In another preferred embodiment, in step (a), the added polyA tail is formed by using polyA polymerase to add AMP to 3' end of miRNA.

In another preferred embodiment, the polyA tail has 8-200 A, preferably 10-100 A, most preferably 12-50 A.

In another preferred embodiment, the miRNA is RNA molecule having 15-200 nucleotides (preferably 18-100 bp) in length. Preferably, the miRNA is non-coding RNA.

In another preferred embodiment, the polyA tail in the method can be replaced by other polyN tail selected from the following group: poly(C) tail, Poly(G) tail or poly(U) tail; and in step (b), a primer which is complementary or substantially complementary to polyN tail of the miRNA is added to anneal the primer and the miRNA containing added polyN tail; and in step (c), the miRNA containing added polyN tail is reverse-transcribed to form cDNA.

In the second aspect of the present invention, a method for improving binding specificity between primer and template during PCR reaction is provided, comprising the following step: adding EvaGreen® fluorescence dye in PCR reaction system.

In another preferred embodiment, the optical density value of EvaGreen® fluorescence dye at 475 nm is between 0.01 and 2 in the reaction system.

In the third aspect of the present invention, a use of EvaGreen® fluorescence dye is provided as a reagent for improving binding specificity between primer and template during PCR reaction.

In the fourth aspect of the present invention, a use of EvaGreen® fluorescence dye is provided to prepare a reagent for improving binding specificity between primer and template during PCR reaction.

In the fifth aspect of the present invention, a method for obtaining the information of non-coding RNA from a sample to be detected, comprising the following steps:

(a) extracting RNA sample containing the non-coding RNA from a sample to be detected;

(b) adding a polyA tail to 3' end of the non-coding RNA for the extracted RNA in step (a);

(c) adding a primer which is complementary to the polyA tail of the non-coding RNA to anneal the primer with the non-coding RNA containing polyA;

(d) reverse-transcribing the non-coding RNA containing polyA tail into cDNA;

(e) conducting PCR amplification to the cDNA, using forward and reverse primers complementary to the cDNA in the PCR reaction system containing EvaGreen® fluorescent dye, thereby forming double stranded DNA-EvaGreen® fluorescent dye complex; and detecting the presence and/or the amount of the amplified products during or after the amplification to obtain information of the non-coding RNA including the presence and the amount of the non-coding RNA in the sample.

In another preferred embodiment, the detection is performed using real-time fluorescence quantification PCR for detecting real-time fluorescence variation of EvaGreen® dye.

In another preferred embodiment, the polyA tail in the method can be replaced by other polyN tail selected from the following group: poly(C) tail, poly(G) tailor poly(U) tail.

In another preferred embodiment, the obtained information of non-coding RNA can be used to describe the condition or status of some diseases of a subject (including but not limited to mammals, such as human) Especially, the method is suitable for the following situations:

a. during certain stage of a disease, expression of certain non-coding RNA is increased;

b. during certain stage of a disease, expression of certain non-coding RNA is decreased.

The above two situations include expression situation of most non-coding RNAs in certain disease.

It should be understood that, within the scope of the present invention, the technical features specifically described above and below (such as the Examples) can be combined with each other, thereby constituting a new or preferred technical solution which needs not be described one by one.

DESCRIPTION OF THE DRAWINGS

FIG. 7 shows the melting curve of the effect of different fluorescence dye, i.e. EvaGreen® (panel 1) and SYBR Green® (panel 2) on the specific binding (solid line) and non specific binding (dashed line) of primer and template. Wherein, trace 1 (curve 1) shows the negative derivative from fluorescence value of binding of EvaGreen® and primer with specific template versus temperature; trace 3 (curve 3) shows the negative derivative from fluorescence value of binding of SYBR Green® I and primer with specific template versus temperature; trace 2 (curve 2) shows the negative derivative from fluorescence value of binding of EvaGreen® and primer with non-specific template versus temperature; and trace 4 (curve 4) shows the negative derivative from fluorescence value of binding of SYBR Green® I and primer with non-specific template versus temperature.

SPECIFIC MODE FOR CARRYING OUT THE INVENTION

Upon extensive and in-depth research, the inventors surprisingly discovered that EvaGreen®, as a DNA binding dye, can improve the binding specificity between primer and template in PCR reaction. Specifically, compared with another commonly used DNA binding dye SYBR Green®, EvaGreen® showed similar sensitivity but could significantly improve the specificity of the reaction. Therefore, EvaGreen® is more suitable for distinguishing and detecting miRNAs with little difference in structure. On this basis, the present invention developed a new method for detecting miRNA with high specificity.

The invention provided an advantageous method for detecting, classifying and quantifying miRNA. The method for detecting miRNA according to the invention is suitable for detecting microRNAs (miRNAs) or other small molecule of nucleotides such as siRNA.

In the invention, a quantitative PCR method (especially real-time quantitative PCR method) based on EvaGreen® is provided, which is suitable for miRNA detection. The quantitative PCR method based on EvaGreen® further can be used for quantitative detection of mRNA and gene expression.

Terms

As used herein, the term "EvaGreen®", "Eva Green®" or "EvaGreen® dye" can be used interchangeably, and refers to a DNA binding dye with trademark "EvaGeen®" produced by Biotium Inc. It is a dye that could be used in real-time PCR and high resolution melting curve (HRM) analysis. Such dye selectively binds to double stranded DNA via a so-called "release-on-demand" mechanism. Such mechanism ensures low PCR inhibition and allows high resolution melting curve (HRM) analysis under the saturated concentration of dye. Because EvaGreen® is similar to FAM and SYBR Green® I in the spectral characteristic, EvaGreen® could be used in all commercial qPCR instruments. In addition, compared with SYBR Green® I and SYBR GreenER, EvaGreen® dye is very stable, non-mutagenic and non-cytotoxic.

The structure of EvaGreen® dye was described in, for example, U.S. Pat. No. 7,776,567.

As used herein, the term "primer" refers to a general term of oligonucleotide that can match with the template and act as a point of initiation to synthesize DNA strand complementary to the template under the action of DNA polymerase. Primer could be natural RNA, DNA, or any form of natural nucleotide. Primer may even be non-natural nucleotide, such as LNA, or ZNA etc.

The primer is substantially (essentially) complementary to a specific sequence on one strand of the template. Elongation cannot be initiated unless the primer is sufficiently complementary to one strand of the template, however, the primer sequence need not be completely complementary to the template sequence. For example, if a sequence which is not complementary to the template is added to 5' end of the primer, 3' end of which is complementary to the template, the resulting primer is still substantially complementary to the template. The primer which is not completely complementary to the template may also form primer-template complex with the template to initiate amplification, so long as the primer is long enough to sufficiently bind to the template.

As used herein, the term "poly(A) polymerase" is an enzyme that is used to add several to hundreds of AMP to 3' hydroxyl end of RNA by using ATP as substrate. Poly(A) polymerase could be extracted from prokaryotic or eukaryotic organisms. Because of low specificity, such enzyme can add several to hundreds of CMP, GMP or UMP to 3' hydroxyl end of RNA by separately using CTP, GTP or UTP as substrate. If poly (C) tail, poly (G) tail or poly (U) tail is added to non-coding RNA, the primer complementary to tail will also be changed accordingly in the invention. Poly(U) polymerase is different from poly(A) polymerase, but has similar function. It can use UTP as substrate to add several to hundreds of UMP to 3' hydroxyl end of RNA. It can also non-specifically use ATP, CTP or GTP, respectively as substrate and add several to hundreds of AMP, CMP or GMP to 3' hydroxyl end of RNA. Therefore, in the invention, poly(U) polymerase and poly(A) polymerase perform the same function.

As used herein, the term "polyA tail" is oligoA or polyA (AMP, adenylic acid) added to the 3' end of RNA during the first step in the invention. The polyA tail could also be replaced by "polyC tail", "polyG tail" or "polyU tail". Accordingly, the primer sequence which is complementary to or substantially complementary to the tail and added during the next step will also be changed. "PolyA tail" could also be added by RNA ligase.

Figure 1:
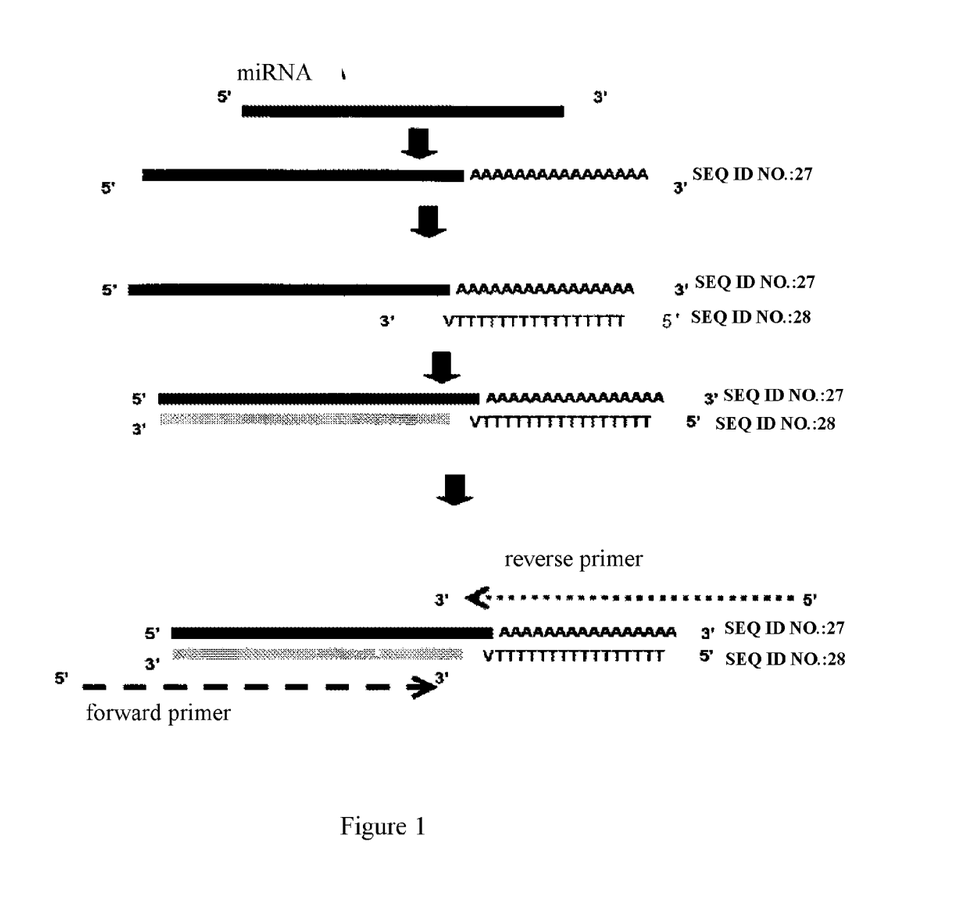
FIG. 1 shows a procedure for miRNA detection by using EvaGreen®-based real-time fluorescence quantitative method. Each step from top to bottom in turn is: adding poly(A) tail; annealing RT primer with RNA; reverse transcription reaction; and conducting PCR amplification by using forward and reverse primers.

Referring to FIG. 1, one preferred technical solution of the invention involves the following steps:

(1) extracting total RNA from the sample that may or may not contain miRNA; and adding AMP to 3' end of miRNA by polymerization under the catalysis of poly (A) polymerase to form miRNA with a polyA tail;

(2) adding a primer complementary to polyA and annealing;

(3) reverse-transcribing miRNA into cDNA under the catalysis of reverse transcriptase;

(4) conducting PCR amplification to cDNA using forward and reverse primers in EvaGreen® fluorescence dye-contained PCR reaction mixed mother liquid;

(5) monitoring real-time change in fluorescence value of EvaGreen® dye during the amplification.

Figure 2:
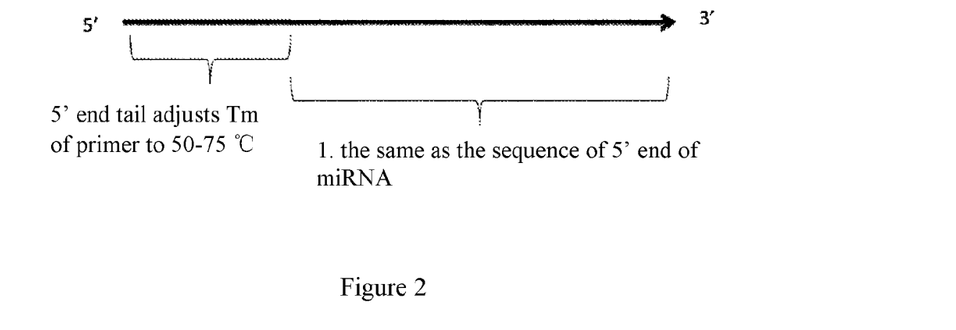
FIG. 2 shows the structure of forward primer in an example of the invention.
Figure 3:
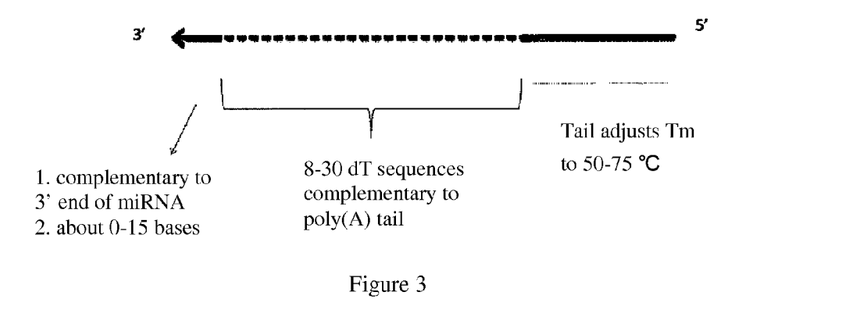
FIG. 3 shows the structure of reverse primer in an example of the invention.

The structures of preferred primer in the present invention are shown in FIG. 2 and FIG. 3.

Generally, the forward primer can be divided into two parts. The 3' end part of the primer is completely complementary to 5' end of miRNA template in such a way that the annealing temperature is 45-65° C., and the added sequence (tail) of another part of the primer, i.e., 5' end, allows the annealing temperature of the whole primer reach 50-75° C.

The reverse primer is comprised of three parts. In the first part, i.e. 3' end of the primer, there are 0 to 15 bases that are completely complementary to 3' end of miRNA; in the middle part of the primer, there are 10 to 30 bases (10 to 30 dT) that is complementary to the added poly(A) tail; and, in the third part, there is an added sequence (tail) having 0 to 40 bases (FIG. 3). It should be understood that the reverse primer is comprised of two parts when the third part 3 is of 0 bases.

PCR reaction requires a reaction mother liquid containing EvaGreen®. The reaction procedure can be carried out in common two-temperature process (e.g. denaturing at 95° C.; annealing and extending at 60° C.) or three-temperature process (e.g. denaturing at 95° C.; annealing at 50° C. and extending at 72° C.). It is necessary to perform the reactions in the presence of a buffer system containing magnesium ion, dNTP, and EvaGreen-double stranded DNA binding dye.

The length of miRNA that can be detected by this invention is not specially limited. It usually could be 15-200 bp, preferably 18-100 bp, more preferably 19-40 bp.

The biological sample containing miRNA that can be detected by this invention is not specially limited. It should be understood that the biological sample is a very broad concept, and can be one or more cells, specimen or cultures (including microbial cultures) as well as synthetic samples. Usually, the biological samples may be animal specimen including human specimen, such as fluid, solid specimen like bone or tissue. The samples also may be liquid or solid food or feed and medicaments, such as dairy products, vegetables, meat and meat products, water and the like. The samples may be derived from any domestic or wild animals, such as ungulates, bear, fish, lagomorphs, and rodents, etc.

Application

The detection and quantitation of miRNA is an important tool for the discovery of targeted gene and pathway thereof, the study on disease mechanism, the evaluation for drug safety and efficiency, disease diagnosis and prognosis evaluation. For example, the content of miRNA in different tissues and the change in the content of miRNA in tissues before and after external irritation (physical or chemical treatment) can be compared. miRNA present in plasma and serum also could be used as an important biomarker for tumor classification, disease diagnosis, prediction and prognosis evaluation.

The main advantages of the invention include:
(a) high specificity;
(b) high sensitivity;
(c) Suitable for both high throughput screening and fine screening;
(d) high reproducibility;
(e) low cost.

The invention will be further illustrated with reference to the following specific examples. It is to be understood that these examples are only intended to illustrate the invention, but not to limit the scope of the invention. For the experimental methods in the following examples without particular conditions, they are performed under routine conditions, for example described in Sambrook et.al. Molecular clone: handbook (New York: Cold Spring Harbor Laboratory Press, 1989) or as instructed by the manufacturer.

EXAMPLES 1

Higher Specificity of EvaGreen® in Real-Time Fluorescence Quantitative PCR

The real-time fluorescence quantitative PCR reaction was carried out by the inventors, wherein $4 \times 10^6$, $4 \times 10^5$, $4 \times 10^4$, $4 \times 10^3$, $4 \times 10^2$, 40, 4, and 0 (NTC) (NTC as non-substrate control) template molecules (hsa-let7a, SEQ ID No: 1 or Table 1), forward primer (SEQ ID No: 9 or Table 1) and reverse primer (SEQ ID No: 10 or Table 1) as well as EvaGreen®-containing PCR reaction mother liquid were used.

TABLE 1 the sequences of miRNA and primer

| Name | SEQ ID No. | Sequence (5'-3') |
|---|---|---|
| hsa-let-7a | 1 | UGAGGUAGUAGGUUGUAUAGUU |
| hsa-let-7b | 2 | UGAGGUAGUAGGUUGUGUGGUU |
| hsa-let-7c | 3 | UGAGGUAGUAGGUUGUAUGGUU |
| hsa-let-7d | 4 | AGAGGUAGUAGGUUGCAUAGUU |
| hsa-let-7e | 5 | UGAGGUAGGAGGUUGUAUAGUU |
| hsa-let-7f | 6 | UGAGGUAGUAGAUUGUAUAGUU |
| hsa-let-7g | 7 | UGAGGUAGUAGUUUGUACAGUU |
| hsa-let-7i | 8 | UGAGGUAGUAGUUUGUGCUGUU |
| let-7a forward primer | 9 | CCCCGTGAGGTAGTAGGTTGTATA |
| let-7b forward primer | 10 | CCGGAGGTAGTAGGTTGTGT |
| let-7c forward primer | 11 | GCCGGTAGTAGGTTGTATGGT |
| let-7d forward primer | 12 | CCCCAGGTAGTAGGTTGCAT |
| let-7e forward primer | 13 | CGGGAGGTAGGAGGTTGTAT |
| let-7f forward primer | 14 | CCCCCTGAGGTAGTAGATTGTATAG |
| let-7g forward primer | 15 | CCCCGTGAGGTAGTAGTTTGTAC |
| let-7i forward primer | 16 | CGGGAGGTAGTAGTTTGTGC |
| let-7a reverse primer | 17 | GATATTCGCACGCATTTTTTTTTTTTAAC |
| let-7b reverse primer | 18 | TCGCACGCATTTTTTTTTTTTAACC |
| let-7c reverse primer | 19 | GGATATTCGCACGCATTTTTTTTTTTTA |
| let-7d reverse primer | 20 | GATATTCGCACGCATTTTTTTTTTTTAACT |
| let-7e reverse primer | 21 | GATATTCGCACGCATTTTTTTTTTTTAACT |
| let-7f reverse primer | 22 | GGATATTCGCACGCATTTTTTTTTTTTAA |
| let-7g reverse primer | 23 | GATATTCGCACGCATTTTTTTTTTTTAACT |
| let-7i reverse primer | 24 | ATATTCGCACGCATTTTTTTTTTTTAACA |
| c7a | 25 | AACTATACTTCCTACTACCTCT |
| c7e | 26 | AACTATACTTCCTCCTACCTCT |

Figure 4:
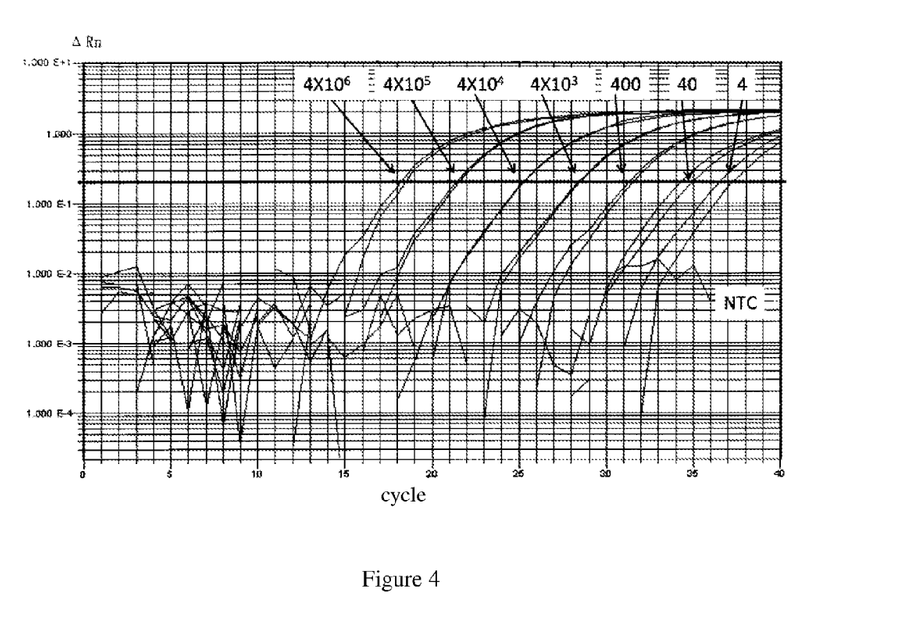
FIG. 4 shows amplification curves for let-7a template at various concentrations.
Figure 5:
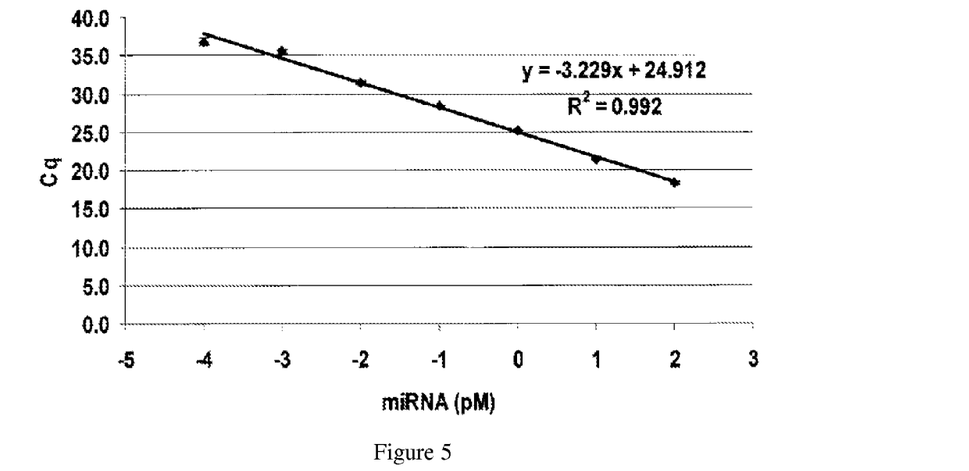
FIG. 5 shows a linear relationship between the amount of miRNA and Cq value.
Figure 6:
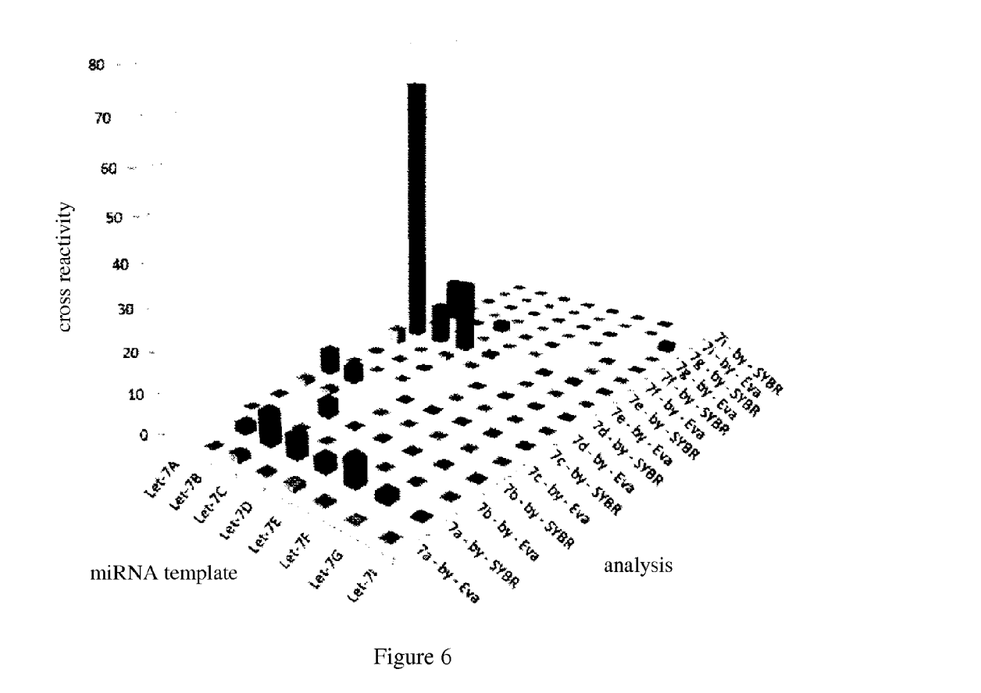
FIG. 6 shows a comparison result of sensitivity and specificity of cross reaction between SYBR Green® I-based and EvaGreen™-based fluorescence quantitative PCR methods.

The results are shown in FIG. 4, FIG. 5 and FIG. 6. The sensitivity, linearity, and dynamic range of the template are shown in FIG. 5.

In the experiment for testing the specificity of EvaGreen®-containing PCR, for eight miRNAs members (the sequences shown in SEQ ID Nos: 1-8 or in Table 1) from human let 7 family, PCR reaction was performed by separately using $4\times10^6$ copies of miRNAs as templates and specific PCR primer pairs (the sequences shown in SEQ ID Nos: 9-24 or in Table 1) and the specificity and sensitivity of PCR reaction of each miRNA member for each different PCR primer were detected.

In the present example, two double stranded DNA-binding dyes, i.e. EvaGreen® and SYBR Green®, were used, and the specificity and sensitivity thereof were compared. If the Ct value for the reaction in the same family is one Ct value lower than that in the different family, the reactivity to the different family corresponds to 50% of the reactivity to the same family, i.e. the cross reactivity thereof is 50%. Similarly, if the Ct value for the reaction in the same family is two Ct value lower than that in the different family, the reactivity to the different family corresponds to 25% of the reactivity to the same family, i.e. the cross reactivity thereof is 25%. By that analogy, if the Ct value for the reaction in the same family is three Ct value lower than that in the different family, the reactivity to the different family corresponds to 12.5% of the reactivity to the same family, i.e. the cross reactivity thereof is 12.5%; and if the Ct value for the reaction in the same family is four Ct value lower than that in the different family, the reactivity to the different family corresponds to 6.25% of the reactivity to the same family, i.e. the cross reactivity thereof is 6.25%. For miRNA detection experiment, less than 5% of cross reactivity is generally acceptable.

In the present example, two double stranded DNA-binding dyes, i.e. EvaGreen® and SYBR Green®, were used, and the specificity and sensitivity of real-time fluorescence quantitative PCR reaction to eight miRNAs members from human let 7 family were compared.

The results are summarized in FIG. 6. In 49 cross reactions, eight SYBR Green® dye-based quantitative PCR reactions have more than 5% of cross reactivity, wherein the worst is over 70%. In contrast, none of EvaGreen dye-based reactions shows more than 5% of cross reactivity. So the specificity of EvaGreen™-based real-time fluorescence quantitative PCR is higher than that based on SYBR Green®.

As well known, it is especially important to have specific primer which can distinguish different miRNAs, since miRNAs are very short and very similar in the sequence.

From FIG. 6, table 2A and 2B, it can be surprisingly discovered that the total relative value for characterizing non-specific cross reactivity is 15.1 (table 2A) in EvaGreen®-based reaction. On the contrary, the total relative value for characterizing non-specific cross reaction reach 161 (table 2B) in SYBR Green-based reaction. In other words, for the same primer pair and miRNA, SYBR Green®-base cross reactivity is ten times higher (161.3, 14.8=10.89) than EvaGreen™-based cross reactivity. That is, using EvaGreen® can improve the specificity by one order of magnitude.

TABLE 2A

EvaGreen ® test results

| primer | miRNA | | | | | | | | | non-specific reaction | specific reaction |
|---|---|---|---|---|---|---|---|---|---|---|---|
| | let-7a | let-7b | let-7c | let-7d | let-7e | let-7f | let-7g | let-7i | NTC | | |
| Let-7A | 100 | 0.0 | 1.8 | 0.6 | 1.4 | 0.8 | 0.0 | 0.0 | 0.0 | 4.6 | 100 |
| Let-7B | 0.0 | 100 | 0.3 | 0.0 | 0.0 | 0.0 | 0.0 | 0.0 | 0.0 | 0.3 | 100 |
| Let-7C | 1.4 | 1.3 | 100 | 0.0 | 0.0 | 0.1 | 0.0 | 0.0 | 0.0 | 2.8 | 100 |
| Let-7D | 0.2 | 0.0 | 0.0 | 100 | 0.0 | 0.0 | 0.0 | 0.0 | 0.0 | 0.2 | 100 |
| Let-7E | 4.1 | 0.0 | 1.2 | 0.4 | 100 | 0.1 | 0.2 | 0.0 | 0.0 | 6.0 | 100 |
| Let-7F | 0.8 | 0.0 | 0.1 | 0.0 | 0.0 | 100 | 0.0 | 0.0 | 0.0 | 0.9 | 100 |
| Let-7G | 0.0 | 0.0 | 0.0 | 0.0 | 0.0 | 0.0 | 100 | 0.0 | 0.0 | 0.0 | 100 |
| Let-7I | 0.0 | 0.0 | 0.0 | 0.0 | 0.0 | 0.0 | 0.0 | 100 | 0.0 | 0.0 | 100 |
| In total | | | | | | | | | | 14.8 | |

TABLE 2B

SYBR Green ® test results

| primer | miRNA | | | | | | | | | non-specific reaction | specific reaction |
|---|---|---|---|---|---|---|---|---|---|---|---|
| | let-7a | let-7b | let-7c | let-7d | let-7e | let-7f | let-7g | let-7i | NTC | | |
| Let-7A | 100 | 2.4 | 8.3 | 5.6 | 3.5 | 6.5 | 2.2 | 0.0 | 0.0 | 28.5 | 100 |
| Let-7B | 0.1 | 100 | 4.1 | 0.0 | 0.1 | 0.0 | 0.0 | 0.0 | 0.0 | 4.3 | 100 |
| Let-7C | 6.4 | 4.4 | 100 | 0.1 | 0.1 | 0.1 | 0.1 | 0.0 | 0.0 | 11.2 | 100 |
| Let-7D | 0.2 | 0.0 | 0.1 | 100 | 0.0 | 0.0 | 0.0 | 0.0 | 0.0 | 0.3 | 100 |
| Let-7E | 70.3 | 10.5 | 18.7 | 0.9 | 100 | 0.3 | 0.4 | 0.0 | 0.0 | 101.1 | 100 |
| Let-7F | 11.1 | 0.0 | 2.4 | 0.0 | 0.0 | 100 | 0.0 | 0.0 | 0.0 | 13.5 | 100 |
| Let-7G | 0.1 | 0.0 | 0.0 | 0.0 | 0.0 | 0.0 | 100 | 2.0 | 0.0 | 2.1 | 100 |
| Let-7I | 0.0 | 0.0 | 0.0 | 0.0 | 0.0 | 0.0 | 0.3 | 100 | 0.0 | 0.3 | 100 |
| In total | | | | | | | | | | 161.3 | |

In table 2A and 2B, let-7a represents miRNA let-7a, and Let-7A represents specific primer pair for miRNA let-7a, and so on. NTC represents non-template.

Wherein, the activity value of pairing reaction using specific primer is set as 100, and the activity value of cross reaction is a ratio relative to the activity value of pairing reaction.

Results:

The sensitivity for miRNA detection in the example using EvaGreen® or SYBR Green® is similar to each other, while specificity is much higher using EvaGreen® compared with SYBR Green®.

EXAMPLE 2

Annealing Experiment Demonstrated EvaGreen® with Higher Specificity

EvaGreen® dye (group A) and SYBR Green® dye (group B) was used respectively. 500 nm of let-7e forward primer (SEQ ID No: 13) with 500 nM c7e (SEQ ID No: 26) formed perfectly matched double stranded structure (curve 1, 3). 500 nM of c7a (SEQ ID No: 25) was used as control to form non-specific double stranded structure with let-7e forward primer (curve 2, 4). The reaction was conducted in 50 mM of Tris (pH 8.0) containing 2.5 mM $MgCl_2$.

Figure 7:
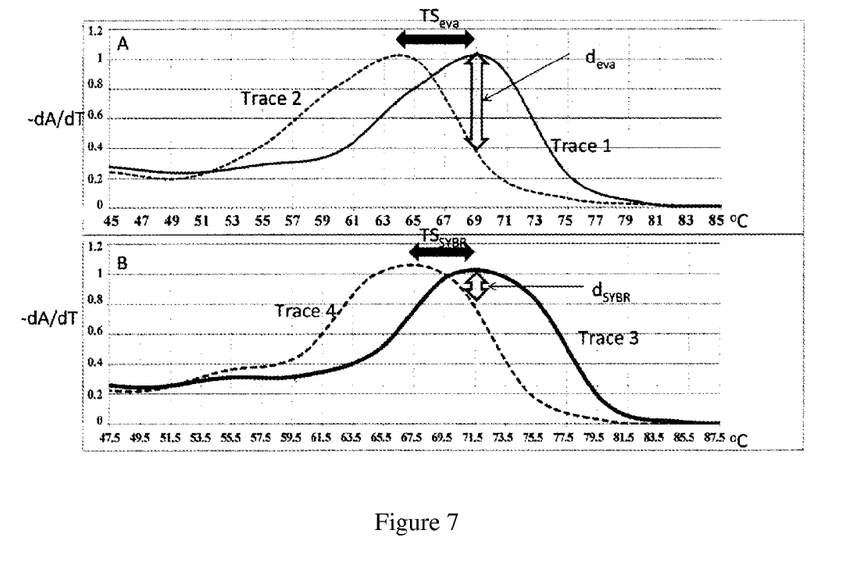

The results are showed in FIG. 7. The temperature peak of annealing curve for the double stranded structure resulted from specific binding is higher than that for the double stranded structure resulted from non-specific binding, whether EvaGreen® or SYBR Green® is used, demonstrating that the annealing temperature for specific binding is higher than that for non-specific binding. However, the difference in temperature between the curve peak of specific binding and non-specific binding for using EvaGreen® ($TS_{eva}$) is significantly greater than that for using SYBR Green® I ($TS_{SYBR}$). The experimental parameter demonstrates that the specificity of primer is higher in the reaction using EvaGreen® dye.

Moreover, $d_{eva}$ represents the drop of fluorescent between trace 1 and trace 2 when trace 1 reaches the temperature peak; and $d_{SYBR}$ represents the drop of fluorescent between trace 3 and trace 4 when trace 3 reaches the temperature peak. The greater the drop is, the greater the difference in two binding situations is, in other words, the smaller the drop is, the smaller the difference in two binding situations is. $d_{eva}$ is greater than $d_{SYBR}$, which indicates that non-specific binding using EvaGreen® is less than that using SYBR Green®. These two annealing experiment parameters further verifies the phenomenology observed in PCR experiment from two perspectives, and demonstrates that the discovery in the invention have physical foundation.

In summary, the annealing experiment further demonstrates that the method using EvaGreen® will have higher specificity in annealing, compared with the method using SYBR Green®.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

---

The invention claimed is:

1. A method for detecting miRNA, the method comprising the following steps:
   (a) adding a polyA tail to the 3' end of miRNA for a miRNA sample to be detected;
   (b) adding a primer which is complementary or substantially complementary to the polyA tail of miRNA to anneal the primer with miRNA containing the added polyA tail;
   (c) reverse-transcribing miRNA containing the added polyA tail into cDNA;
   (d) conducting PCR amplification to the cDNA, using forward and reverse primers complementary to the cDNA in a PCR reaction system containing a fluorescent dye, thereby forming double stranded DNA-fluorescent dye complex; and detecting the amount of the amplified products during or after the amplification to determine the presence and/or the amount of miRNA to be detected, wherein the forward primer has the following characteristics:
   (i) the sequence of 3' end of the forward primer is the same or substantially the same as that of 5' end of the miRNA to be detected; and the Tm value of the sequence of 3' end with cDNA is 45-65° C.;
   (ii) the sequence of the 5' end of the forward primer makes the Tm of the whole forward primer with cDNA between 45° C. and 75° C.; and
   (iii) the length of the forward primer is between 8 bp and 50 bp;

and the reverse primer has the following characteristics:
   (i) 3' end of the reverse primer contains a first complementary region that is complementary to the sequence of 3' end of miRNA to be detected and consists of 1 to 15 bases;
   (ii) the middle sequence of the reverse primer is polyT having 8 to 30 bases in length;
   (iii) the sequence of 5' end of the reverse primer makes the Tm value of the whole reverse primer with cDNA reach 45-75° C.; and
   (iv) the length of the reverse primer is 12-50 bp;
   wherein the forward primer and the reverse primer is selected from the group consisting of SEQ ID Nos.: 9-24.

2. A method for obtaining the information of non-coding RNA from a sample to be detected, wherein the method comprises the following steps:
   (a) extracting RNA sample containing the non-coding RNA from a sample to be detected;
   (b) adding a poly A tail to 3' end of the non-coding RNA for the extracted RNA in step (a);
   (c) adding a primer which is complementary to the polyA tail of the non-coding RNA to anneal the primer with the non-coding RNA containing polyA;

(d) reverse-transcribing the noncoding RNA containing polyA tail into cDNA;

(e) conducting PCR amplification to the cDNA, using forward and reverse primers complementary to the cDNA in the PCR reaction system containing a fluorescent dye, thereby forming double stranded DNA-fluorescent dye complex; and detecting the presence and/or the amount of the amplified products during or after the amplification to obtain information of the non-coding RNA including the presence and the amount of the non-coding RNA in the sample, wherein the forward primer has the following characteristics:

(i) the sequence of 3' end of the forward primer is the same or substantially the same as that of 5' end of the miRNA to be detected; and the Tm value of the sequence of 3' end with cDNA is 45-65° C.;

(ii) the sequence of 5' end of the forward primer makes the Tm value of the whole forward primer with cDNA reach 45-75° C.; and (iii) the length of the forward primer is 8-50 bp;

and the reverse primer has the following characteristics:

(i) 3' end of the reverse primer contains a first complementary region that is complementary to the sequence of 3' end of miRNA to be detected and consists of 1 to 15 bases;

(ii) the middle sequence of the reverse primer is polyT having 8 to 30 bases in length;

(iii) the sequence of 5' end of the reverse primer makes the Tm value of the whole reverse primer with cDNA reach 45-75° C.; and (iv) the length of the reverse primer is 12-50 bp;

wherein the forward primer and the reverse primer is selected from the group consisting of SEQ ID Nos.: 9-24.

3. A method for improving binding specificity between a primer and a template during PCR reaction, wherein the method comprises the step of adding the primer and a fluorescence dye in PCR reaction system, wherein the primer comprises a forward primer and a reverse primer;

wherein, the forward primer has the following characteristics:

(i) the sequence of 3' end of the forward primer is the same or substantially the same as that of 5' end of the miRNA to be detected; and the Tm value of the sequence of 3' end with cDNA is 45-65° C.;

(ii) the sequence of 5' end of the forward primer makes the Tm value of the whole forward primer with cDNA reach 45-75° C.; and (iii) the length of the forward primer is 8-50 bp; and the reverse primer has the following characteristics:

(i) 3' end of the reverse primer contains a first complementary region that is complementary to the sequence of 3' end of miRNA to be detected and consists of 1 to 15 bases;

(ii) the middle sequence of the reverse primer is polyT having 8 to 30 bases in length;

(iii) the sequence of 5' end of the reverse primer makes the Tm value of the whole reverse primer with cDNA reach 45-75° C.; and (iv) the length of the reverse primer is 12-50 bp;

wherein the forward primer and the reverse primer is selected from the group consisting of SEQ ID Nos.: 9-24.

4. The method according to claim 3, wherein the fluorescence dye is a DNA binding dye.

5. The method according to claim 1, wherein, in step (d), the amount of the amplified products is determined by detecting the fluorescence value of the fluorescent dye.

6. The method according to claim 1, wherein the forward primer has the following characteristics:

(i) the sequence of 3' end of the forward primer is the same as that of 5' end of the miRNA to be detected; and (ii) the sequence of 5' end of the forward primer makes the Tm value of the whole forward primer with cDNA reach 50-75° C.

7. The method according to claim 1, wherein the sample to be detected is selected the following group: animal sample, food, fodder and medicament.

8. The method according to claim 1, wherein the fluorescence dye is a DNA binding dye.

9. The method according to claim 1, wherein the fluorescence dye is N',N'-dimethyl-N-[4-[(E)-(3-methyl-1,3-benzothiazol-2-ylidene)methyl]-1-phenylquinolin-1-ium-2-yl]-N-propylpropane-1,3-diamine.

\* \* \* \* \*

SEQUENCE LISTING

```
<160> NUMBER OF SEQ ID NOS: 28

<210> SEQ ID NO 1
<211> LENGTH: 22
<212> TYPE: RNA
<213> ORGANISM: Homo sapiens

<400> SEQUENCE: 1
ugagguagua gguuguauag uu                                              22

<210> SEQ ID NO 2
<211> LENGTH: 22
<212> TYPE: RNA
<213> ORGANISM: Homo sapiens

<400> SEQUENCE: 2
ugagguagua gguugugugg uu                                              22

<210> SEQ ID NO 3
<211> LENGTH: 22
<212> TYPE: RNA
<213> ORGANISM: Homo sapiens

<400> SEQUENCE: 3
ugagguagua gguuguaugg uu                                              22

<210> SEQ ID NO 4
<211> LENGTH: 22
<212> TYPE: RNA
<213> ORGANISM: Homo sapiens
```

```
<400> SEQUENCE: 4
agagguagua gguugcauag uu                                              22

<210> SEQ ID NO 5
<211> LENGTH: 22
<212> TYPE: RNA
<213> ORGANISM: Homo sapiens

<400> SEQUENCE: 5
ugagguagga gguuguauag uu                                              22

<210> SEQ ID NO 6
<211> LENGTH: 22
<212> TYPE: RNA
<213> ORGANISM: Homo sapiens

<400> SEQUENCE: 6
ugagguagua gauuguauag uu                                              22

<210> SEQ ID NO 7
<211> LENGTH: 22
<212> TYPE: RNA
<213> ORGANISM: Homo sapiens

<400> SEQUENCE: 7
ugagguagua guuuguacag uu                                              22

<210> SEQ ID NO 8
<211> LENGTH: 22
<212> TYPE: RNA
<213> ORGANISM: Homo sapiens

<400> SEQUENCE: 8
ugagguagua guuugugcug uu                                              22

<210> SEQ ID NO 9
<211> LENGTH: 24
<212> TYPE: DNA
<213> ORGANISM: Artificial sequence
<220> FEATURE:
<223> OTHER INFORMATION: Primer

<400> SEQUENCE: 9
ccccgtgagg tagtaggttg tata                                            24

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
ccggaggtag taggttgtgt                                                 20

<210> SEQ ID NO 11
<211> LENGTH: 21
<212> TYPE: DNA
<213> ORGANISM: Artificial sequence
<220> FEATURE:
<223> OTHER INFORMATION: Primer

<400> SEQUENCE: 11
gccggtagta ggttgtatgg t                                               21
```

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
ccccaggtag taggttgcat                                               20

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13
cgggaggtag gaggttgtat                                               20

<210> SEQ ID NO 14
<211> LENGTH: 25
<212> TYPE: DNA
<213> ORGANISM: Artificial sequence
<220> FEATURE:
<223> OTHER INFORMATION: Primer

<400> SEQUENCE: 14 cccccctgagg tagtagattg tatag                                        25

<210> SEQ ID NO 15
<211> LENGTH: 23
<212> TYPE: DNA
<213> ORGANISM: Artificial sequence
<220> FEATURE:
<223> OTHER INFORMATION: Primer

<400> SEQUENCE: 15
ccccgtgagg tagtagtttg tac                                           23

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
cgggaggtag tagtttgtgc                                               20

<210> SEQ ID NO 17
<211> LENGTH: 31
<212> TYPE: DNA
<213> ORGANISM: Artificial sequence
<220> FEATURE:
<223> OTHER INFORMATION: Primer

<400> SEQUENCE: 17
gatattcgca cgcatttttt tttttttaa c                                   31

<210> SEQ ID NO 18
<211> LENGTH: 27
<212> TYPE: DNA
<213> ORGANISM: Artificial sequence
<220> FEATURE:

<223> OTHER INFORMATION: Primer

<400> SEQUENCE: 18
tcgcacgcat tttttttttt tttaacc                                27

<210> SEQ ID NO 19
<211> LENGTH: 30
<212> TYPE: DNA
<213> ORGANISM: Artificial sequence
<220> FEATURE:
<223> OTHER INFORMATION: Primer

<400> SEQUENCE: 19
ggatattcgc acgcattttt ttttttttta                             30

<210> SEQ ID NO 20
<211> LENGTH: 32
<212> TYPE: DNA
<213> ORGANISM: Artificial sequence
<220> FEATURE:
<223> OTHER INFORMATION: Primer

<400> SEQUENCE: 20
gatattcgca cgcatttttt ttttttttaa ct                          32

<210> SEQ ID NO 21
<211> LENGTH: 32
<212> TYPE: DNA
<213> ORGANISM: Artificial sequence
<220> FEATURE:
<223> OTHER INFORMATION: Primer

<400> SEQUENCE: 21
gatattcgca cgcatttttt ttttttttaa ct                          32

<210> SEQ ID NO 22
<211> LENGTH: 31
<212> TYPE: DNA
<213> ORGANISM: Artificial sequence
<220> FEATURE:
<223> OTHER INFORMATION: Primer

<400> SEQUENCE: 22
ggatattcgc acgcattttt ttttttttta a                           31

<210> SEQ ID NO 23
<211> LENGTH: 32
<212> TYPE: DNA
<213> ORGANISM: Artificial sequence
<220> FEATURE:
<223> OTHER INFORMATION: Primer

<400> SEQUENCE: 23
gatattcgca cgcatttttt ttttttttaa ct                          32

<210> SEQ ID NO 24
<211> LENGTH: 31
<212> TYPE: DNA
<213> ORGANISM: Artificial sequence
<220> FEATURE:
<223> OTHER INFORMATION: Primer

<400> SEQUENCE: 24
atattcgcac gcattttttt ttttttaac a                            31

-continued

```
<210> SEQ ID NO 25
<211> LENGTH: 22
<212> TYPE: DNA
<213> ORGANISM: Artificial sequence
<220> FEATURE:
<223> OTHER INFORMATION: oligonucleotide

<400> SEQUENCE: 25
aactatactt cctactacct ct                                            22

<210> SEQ ID NO 26
<211> LENGTH: 22
<212> TYPE: DNA
<213> ORGANISM: Artificial sequence
<220> FEATURE:
<223> OTHER INFORMATION: oligonucleotide

<400> SEQUENCE: 26
aactatactt cctcctacct ct                                            22

<210> SEQ ID NO 27
<211> LENGTH: 16
<212> TYPE: DNA
<213> ORGANISM: Artificial sequence
<220> FEATURE:
<223> OTHER INFORMATION: oligonucleotide

<400> SEQUENCE: 27
aaaaaaaaaa aaaaaa                                                   16

<210> SEQ ID NO 28
<211> LENGTH: 17
<212> TYPE: DNA
<213> ORGANISM: Artificial sequence
<220> FEATURE:
<223> OTHER INFORMATION: oligonucleotide

<400> SEQUENCE: 28
tttttttttt tttttv                                                   17
```